United States Patent
Kobayashi

(10) Patent No.: US 6,858,033 B2
(45) Date of Patent: Feb. 22, 2005

(54) INSERTION SYSTEM FOR INTRAOCULAR LENS

(75) Inventor: Kenichi Kobayashi, Tokyo (JP)

(73) Assignee: Canon-Staar Co., Inc., Tokyo (JP)

(*) Notice: Subject to any disclaimer, the term of this patent is extended or adjusted under 35 U.S.C. 154(b) by 285 days.

(21) Appl. No.: 10/256,933

(22) Filed: Sep. 27, 2002

(65) Prior Publication Data

US 2003/0212408 A1 Nov. 13, 2003

(30) Foreign Application Priority Data

May 8, 2002 (JP) ........................... 2002-133183

(51) Int. Cl.[7] .............................................. A61F 9/11
(52) U.S. Cl. .................... 606/107; 623/5.16; 623/6.11; 623/6.12
(58) Field of Search ................ 606/107, 108; 623/5.16, 6.11, 6.12

(56) References Cited

U.S. PATENT DOCUMENTS

| 5,496,328 A | | 3/1996 | Nakajima et al. | |
| 5,860,984 A | * | 1/1999 | Chambers et al. | 606/107 |
| 6,093,193 A | * | 7/2000 | Makker et al. | 606/107 |
| 6,398,788 B1 | * | 6/2002 | Makker et al. | 606/107 |

FOREIGN PATENT DOCUMENTS

| JP | 58-146346 | 8/1983 |
| JP | 2-212350 | 8/1990 |
| JP | 5-103803 | 4/1993 |
| JP | 5-103808 | 4/1993 |
| JP | 5-103809 | 4/1993 |
| JP | 7-23990 | 1/1995 |
| JP | 7-23991 | 1/1995 |
| JP | 7-212350 | 8/1995 |
| JP | 8-38542 | 2/1996 |
| JP | 9-506285 | 6/1997 |
| JP | 11-510711 | 9/1999 |
| JP | 2000-60880 | 2/2000 |
| JP | 2001104347 | 4/2001 |

* cited by examiner

Primary Examiner—Kevin T. Truong
(74) Attorney, Agent, or Firm—Roth & Goldman, P.A.

(57) ABSTRACT

An insertion system for an intraocular lens having a deformable optical portion and loop-shaped support portions for supporting the optical portion within an eye includes a holding member for holding the intraocular lens at a standby position in a state in which no stress acts on the optical portion of the lens; a deforming member for deforming the lens to a reduced size; an insertion tube through which the deformed lens is inserted into the eye; a pusher mechanism having a push rod for pushing and inserting the lens into the eye; and a lens moving mechanism for moving the lens from the standby position to an insertion position at which the pusher mechanism can push and insert the lens into the eye. When the lens is moved to the insertion position, the optical portion and the support portions of the lens are placed in different spaces in order to fix the positional relationship between the optical portion and the support portions of the lens.

3 Claims, 3 Drawing Sheets

INSERTION SYSTEM FOR INTRAOCULAR LENS

BACKGROUND OF THE INVENTION

1. Field of the Invention

The present invention relates to a system for inserting a deformable intraocular lens into the eye. Examples of such a deformable intraocular lens include a deformable intraocular lens that is inserted into the eye in place of the natural lens when the latter is physically extracted because of cataracts, and a vision correction lens that is inserted into the eye for the sole purpose of vision correction.

2. Description of the Related Art

In general, during cataract surgery, an intraocular lens is inserted into the eye, from which the natural lens has been removed (lens-removed eye), such that the intraocular lens is located in the original position previously occupied by the natural lens and restores vision. Various studies on the material and shape of such an intraocular lens have been carried out since Ridley performed the first implantation of an artificial lens in 1949.

In recent years, in addition to studies on intraocular lenses which are used for vision restoration after cataract surgery, intense studies on intraocular lenses for refractivity correction have been ongoing. Such an intraocular lens for refractivity correction is inserted into the eye which still has a natural lens (lens-carrying eye), for correction of nearsightedness or farsightedness.

In relation to cataract surgery, a technique for crushing the lens tissue by means of ultrasonic emulsification and suctioning the crushed tissue away has been popularized. This technique enables performance of lens removal surgery to excise an opaque lens through a small incision. Along with progress in the operational technique itself, intraocular lenses themselves have recently been improved. Such an improved intraocular lens is disclosed in, for example, Japanese Patent Application Laid-Open (kokai) No. 58-146346. In the intraocular lens, the optical portion is made of a deformable elastic material. The intraocular lens is inserted, in a folded state, into the eye through a small incision and restored to its original shape within the eye allowing it to exert its proper lens function.

Accompanying these technical developments, the material of the optical portion of such an intraocular lens has been changed gradually from hard polymethyl methacrylate (PMMA) to silicone or soft acrylic resin, which enables the intraocular lens to be inserted into the eye in a folded state.

Moreover, in recent years, studies have been conducted on copolymers such as hydroxyethyl methacrylate and methyl methacrylate, as well as on hydrophilic materials such as 2-hydroxyethyl methacrylate (HEMA).

Further, intraocular lenses of different shapes have been studied and put into practical use, including an intraocular lens having a circular optical portion and loop-shaped support portions formed of different materials, an intraocular lens whose loop-shaped support portions and optical portion are formed of the same material, and an intraocular lens having plate-shaped support portions.

Furthermore, the following patent publications disclose insertion devices for inserting the above-described deformable intraocular lens into the eye in a compressed or folded state.

(1) Japanese Patent Application Laid-Open (kokai) No. 5-103803 discloses a device designed such that a holding member which holds a folded lens is attached to a main body, and the lens is inserted into the eye through an insertion tube provided at the tip end of the holding member.

(2) Japanese Patent Application Laid-Open (kokai) No. 7-23991 discloses a disposable insertion device for one-time use in which a portion for holding a folded lens is integrated with a main body of the device and the entirety of the device is formed of resin.

(3) Japanese Kohyo (PCT) Patent Publication No. 9-506285 discloses an intraocular-lens insertion device having a broadened range of applications. In the intraocular-lens insertion device, a lens is held in a stress-free state in an intermediate preparation region of a main body. After attachment of a cannulae (insertion tube) to the main body, the intraocular lens is inserted into the eye through the cannulae.

The conventional intraocular-lens insertion devices described in (1) and (2) above have the following drawbacks. When either of these devices is used, an intraocular lens removed from a package is placed on a placement portion of the device, is deformed, and then inserted into the eye. Therefore, during actual operation, work for placing the intraocular lens onto the device is needed, resulting in increased time and labor involved in implantation of the intraocular lens.

Further, such an intraocular lens and insertion device must be made germ-free through a sterilization procedure, because they are inserted into the eye through an incision. However, if an operator accidentally drops the lens and/or the insertion device onto an unclean surface, such as a floor or table, during the placement operation, the germ-free state is lost, and the lens and/or the insertion device becomes unusable.

Further, when the operator forcedly inserts into the eye an intraocular lens which has been placed on the device improperly, the lens may be broken, or may forcibly fly out from the insertion tube, potentially resulting in damage to the internal tissue of the eye.

The intraocular-lens insertion device described in (3) above has the following drawbacks. Although the intermediate region of the device can be used as a lens package, work for attaching a cannulae (insertion tube) to the main body must be performed during actual use, because the cannulae (insertion tube) is a member which is formed separately from the main body. Although the patent publication discloses a technique for storing in advance an intraocular lens at the intermediate region located on the center axis of a push rod, the intermediate region is difficult to be formed from a material suitable for storing the lens. In addition, when the lens has loop-shaped support portions, the positional relationship between the optical portion and the support portions of the lens is unstable. Therefore, when the lens is advanced from the intermediate region by the push rod, the support portions may be rolled in the optical portion with the result that the support portions are deformed.

SUMMARY OF THE INVENTION

An object of the present invention is to provide an insertion system for a deformable intraocular lens, which can stabilize the positional relationship between the optical portion and support portions of the lens and which eliminates the necessity of a conventionally-used lens case for the intraocular lens.

Another object of the present invention is to provide an insertion system for a deformable intraocular lens, which system eliminates or simplifies an operation of placing a lens on an insertion device to thereby save the time involved in the placement operation, while solving drawbacks involved in conventional insertion systems, such as breakage of a lens or improper insertion of a lens, which would otherwise be caused by an improper operation by an operator, and breakage of a lens support portion, which would otherwise be caused by the push rod.

Still another object of the present invention is to provide an insertion system for a deformable intraocular lens, which system enables supply of an intraocular lens and an insertion device in a sterilized sate.

In order to achieve the above objects, the present invention provides an insertion system for an intraocular lens having a deformable optical portion and at least one loop-shaped support portion for supporting the optical portion within an eye. The insertion system includes holding means for holding the intraocular lens at a standby position in a state in which no stress acts on the optical portion of the lens; deforming means for deforming the lens to a reduced size; an insertion tube through which the deformed lens is inserted into the eye; a pusher mechanism having a push rod for pushing and inserting the lens into the eye; and a lens moving mechanism for moving the lens from the standby position to an insertion position at which the pusher mechanism can push and insert the lens into the eye. When the lens is moved to the insertion position by means of the lens moving mechanism, the optical portion and the support portion of the lens are placed in different spaces in order to fix the positional relationship between the optical portion and the support portion of the lens.

By virtue of the above-described configuration, an placement operation for an intraocular lens can be completed by merely moving the lens from the standby position to the insertion position by the moving mechanism. This eliminates a conventionally practiced operation of removing an intraocular lens from a lens case and placing it on the insertion system.

In addition, the insertion system according to the present invention prevents deformation or breakage of the lens support portion, which would otherwise occur due to interference with the tip end of the push rod, and prevents erroneous operation involved in the placement operation to thereby improve safety.

Further, since the insertion system according to the present invention is provided with a mechanism for holding an intraocular lens at the standby position in a desired state, deformation of the lens during storage can be prevented. Moreover, when packaging and sterilization for the insertion device are performed in a sate in which the lens is held in the insertion device, a completely sterilized intraocular-lens insertion system can be provided.

Preferably, the positional relationship between the optical portion and the support portion of the lens is changed along a direction of movement of the lens.

More preferably, when the lens is pushed out by means of the pushing mechanism, the optical portion and the support portion of the lens located in the different spaces move to a common space.

BRIEF DESCRIPTION OF THE DRAWINGS

Various other objects, features and many of the attendant advantages of the present invention will be readily appreciated as the same becomes better understood by reference to the following detailed description of the preferred embodiment when considered in connection with the accompanying drawings, in which:

FIGS. 1A and 1B are views showing an embodiment of the intraocular-lens insertion system according to the present invention, wherein FIG. 1A is a front view of an insertion device showing a state in which a lens holding member has been attached to the insertion device and the intraocular lens is located at a first or standby position, and FIG. 1B is a front view of the insertion device showing a state in which the lens is located at a second or insertion position;

FIGS. 2A and 2B are enlarged views showing a portion of the insertion divide, wherein FIG. 2A shows a state in which the intraocular lens is located at the first or standby position, and FIG. 2B shows a state in which the lens is located at the second or insertion position;

FIGS. 3A and 3B are cross sections of a main portion of the insertion device shown in FIGS. 1A and 1B, wherein FIG. 3A is an enlarged cross section taken along line 3A—3A in FIG. 1A, FIG. 3B is an enlarged cross section taken along line 3B—3B in FIG. 1B, FIGS. 4A and 4B are views showing a conventional device, wherein FIG. 4A is an enlarged cross section corresponding to FIG. 3B, and FIG. 4B is an enlarged view of a portion of FIG. 4A indicated by arrow B.

DETAILED DESCRIPTION OF PREFERRED EMBODIMENT

Figure 1A:
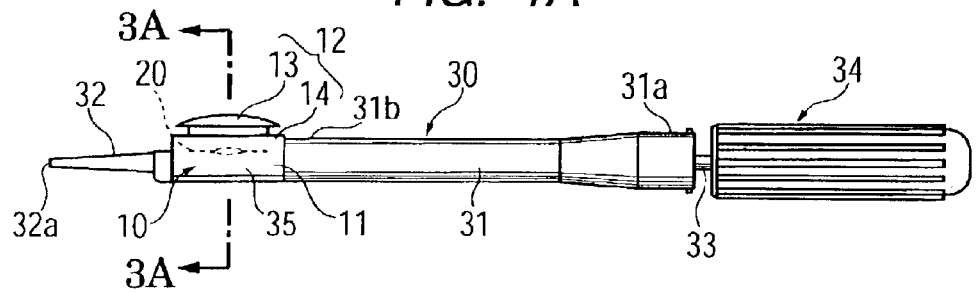
Figure 1B:
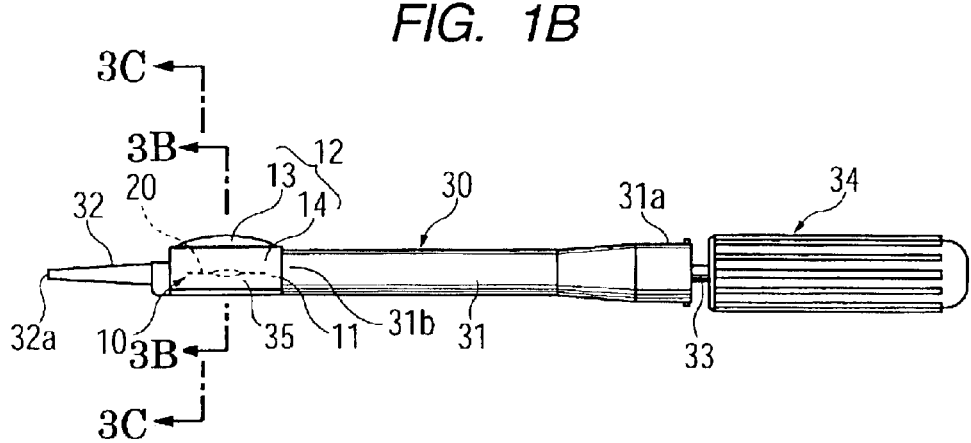

FIGS. 1A and 1B show one embodiment of an intraocular-lens insertion system according to the present invention. In the present embodiment, an intraocular lens 20 horizontally stored in a lens holding member 10 serving as holding means for the intraocular lens 20 can be moved between a first or standby position at which the vertical position of the center of the intraocular lens 20 does not coincide with the center axis of a push rod 33 of an insertion device 30 and a second or insertion position at which the vertical position of the center of the intraocular lens 20 coincides with the center axis of the push rod 33 of the insertion device 30, so that the intraocular lens 20 can be pushed out by the push rod 33. Further, a push member 13 is provided as a lens moving mechanism for moving the intraocular lens 20 from the first or standby position to the second or insertion position.

Figure 2A:
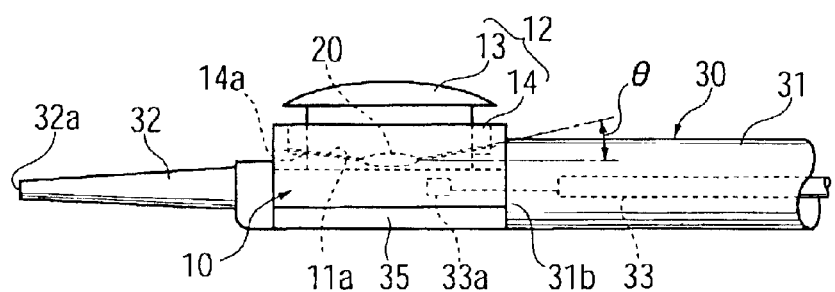
Figure 2B:
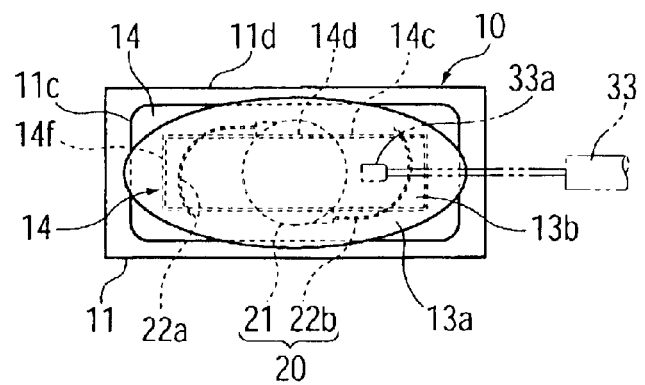

FIG. 1A is a front view of the insertion device 30 to which the lens holding member 10 has been attached and in which the intraocular lens 20 is located at the first or standby position, and FIG. 2B is a front view of the insertion device 30 in which the intraocular lens 20 is located at the second or insertion position.

The system according to the present invention is mainly composed of the lens holding member 10, which serves as lens holding means for storing the intraocular lens 20, and the insertion device 30 for inserting the intraocular lens 20 into the eye of a patient.

The insertion device 30 includes a tubular main body 31, the above-mentioned push rod 33, a pusher mechanism 34, and an attachment portion 35. The tubular main body 31 of the insertion device 30 is formed of transparent or semi-transparent plastic or any other suitable material such that the diameter at the base end 31a is larger than that at the tip end 31b. The push rod 33 is disposed to be located on the center axis of the tubular main body 31. The pusher mechanism 34 is disposed at the rear end 31a of the tubular main body 31 of the insertion device 30 and is coupled to the rear end of the push rod 33 so as to advance and retract the push rod 33. The attachment portion 35 is formed at the tip end 31b of the tubular main body 31 and adapted to receive the lens holding member 10 serving as holding means. A tapered insertion tube 32 is formed at the tip end of the attachment portion 35 such that the through hole of the insertion tube 32 is aligned with the center axis of the tubular main body 31. The intraocular lens 20 is pushed out from the tip end 32a of the insertion tube 32 after being deformed to a reduced size.

In the first or standby position shown in FIG. 1A, the vertical position of the center of the lens does not coincide with the center axis of the push rod 33 represented by an alternate long and short dash line L. The intraocular lens 20 is stored within the lens holding member 10 at the first or standby position shown in FIG. 1A.

When a push member 13 of a top member 12 of the lens holding member 10 is pushed downward in FIG. 1A, the intraocular lens 20 is moved downward to the second or insertion position shown in FIG. 1B, at which the vertical position of the center of the lens substantially coincides with the center axis of the push rod 33.

In this second or insertion position, the intraocular lens 20 can be pushed out from the tip end 32a of the insertion tube 32 into the eye through advance movement of the push rod 33 effected by the pusher mechanism 34 provided at the rear end 31a of the tubular main body 31.

FIGS. 2A and 2B are views showing an assembled state in which the lens holding member 10 has been attached to the insertion device 30, wherein FIG. 2A is an enlarged front view of the insertion device 30 showing a state in which the intraocular lens is located at the first or standby position, and FIG. 2B is an enlarged front view of the insertion device 30 showing a state in which the lens is located at the second or insertion position.

The lens holding member 10 consists of the abovementioned top member 12 and a base member 11 having a structure suitable for supporting the intraocular lens 20 having loop-shaped support portions 22a and 22b made of a material different from that of the optical portion 21. Specifically, the base member 11 has engagement portions 11b which have inclined surfaces 11a of angle θ extending in opposite longitudinal directions and maintaining the angel θ between the optical portion 21 and the support portions 22a and 22b of the intraocular lens 20. The nipping member 14 of the top member 12 has on its bottom surface 14b inclined surfaces 14a to be mated with the inclined surfaces 11a of the base member 11. After placement of the lens 20 on the base member 11, the top member 12 is placed on the base member 11, so that the support portions 22a and 22b of the lens 20 are nipped between the base member 11 and the nipping member 14 of the top member 12.

Figure 3A:
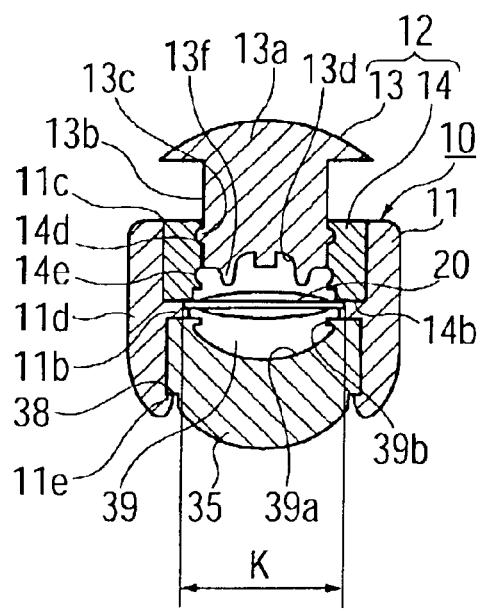
Figure 3B:
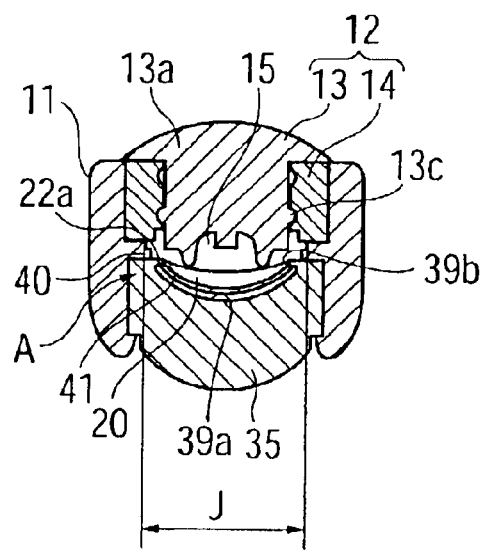

As shown in FIGS. 3A and 3B, the base member 11 of the lens holding member 10 has an opening 11c in the top surface thereof and projections 11e in the vicinity of the lower ends of opposite side walls 11d. The projections 11e elastically engage with engagement steps 38 formed in the vicinity of the lower ends of the lateral side surfaces of the attachment portion 35. The longitudinal opposite ends of the base member 11 are opened so that the base member 11 has a squarish C-like cross section. Further, the paired engagement portions 11b are formed on the inner surfaces of the side walls 11d to be located at the approximate center in the vertical direction. The engagement portions 11b extend in the longitudinal direction and adapted to receive the peripheral portions of the optical portion 21 and the support portions 22a and 22b of the intraocular lens 20. As shown in FIG. 2A, the inclined surfaces 11a each having an inclination angle θ are formed on the engagement portions 11b in order to maintain the angle θ between the optical portion 21 and the support portions 22a and 22b of the intraocular lens 20.

The top member 12 to be inserted into the top surface opening 11c of the base member 11 has the hollow nipping member 14 having a rectangular frame-like shape, and the above-mentioned push member 13 disposed in the nipping member 14 to be movable in the vertical direction. The bottom surface 14b of the nipping member 14 has the inclined surfaces 14a corresponding to the inclined surfaces 11a of the engagement portions 11b of the base member 11. Upper and lower depressions 14d and 14e are formed at a predetermined interval on each of the inner surfaces 14c of the opposite lateral walls such that the upper depressions 14d are opposed to each other and the lower depression 14e are opposed to each other.

The above-mentioned push member 13 is inserted into the opening 14f of the nipping member 14 and is pressed downward in order to move the intraocular lens 20 from the standby position to the insertion position. The push member 13 has a head portion 13a of a large diameter and a prism-shaped leg portion 13b. Protrusions 13c are formed on the peripheral surface thereof and in the vicinity of the lower end thereof so as to be engaged selectively with the upper depressions 14d or the lower depressions 14e of the nipping member 14. Specifically, at the standby position, the protrusions 13c of the push member 13 engage the depressions 14d, and when the push member 13 is pressed, the protrusions 13c move downward and come into engagement with the depressions 14e. A concave surface 13d is formed on the bottom surface of the leg portion 13b, and a ridge 13f for supporting the peripheral portion of the intraocular lens 20 is formed on the concave surface 13d.

As shown in FIG. 3A, the above-described attachment portion 35 has a lens movement portion 39, which has a concavely-curved groove 39a, and opening projection edges 39b provided at the opening of the curved groove 39a. The curved groove 39a provides a space 15 for accommodating the optical portion 21 of the lens 20.

Figure 3C:
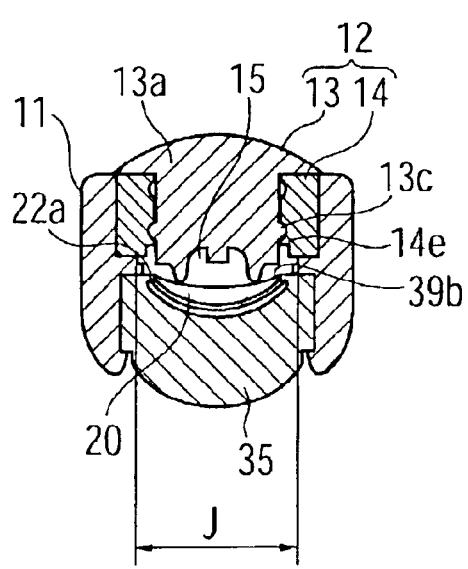
FIG. 3C is an enlarged cross section taken along line 3C—3C in FIG. 1B.
Figure 3D:
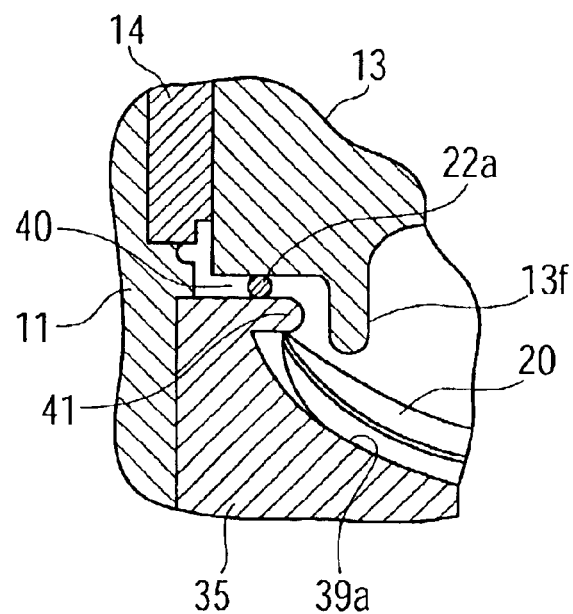
FIG. 3D is an enlarged view of a portion of FIG. 3B indicated by arrow A.

In the present embodiment, as shown in FIG. 3D, the opening projection edges 39b are extended inward to form support portion guides 41 for supporting the supporting portions 22a and 22b of the lens 20. The support portion guides 41 each have a sufficiently large width such that even when the optical portion 21 of the lens 20 is pushed into the curved groove 39a, the support portions 22a and 22b of the lens 20 remain on the support portion guides 41, as shown in FIG. 3D.

Further, the length of the leg portion 13b of the push member 13 is determined in such a manner that even after the push member 13 is completely pressed downward, a space 40 is formed between each of the support portion guides 41 and a lower end surface of the push member 13. The distance between each of the support portion guides 41 and the lower end surface of the push member 13 is made slightly greater than the cross sectional diameter of the support portions 22a and 22b in order to enable smooth movement of the support portions 22a and 22b.

The support portion guides 41 extends from the base end of the attachment portion 35 toward the insertion tube 32 but ends at an axial position before the distal end of the attachment portion 35. Therefore, in FIG. 3C, which is a cross section taken along line 3C—3C of FIG. 1B, the support portion guides 41 are not present.

When the intraocular lens 20 is to be moved from the first or standby position shown in FIG. 3A to the second or insertion position shown in FIG. 3B, the head portion 13a of the push member 13 of the top member 12 is pressed down such that the intraocular lens 20 whose peripheral portion is partially nipped by the base member 11 and the top member 12 of the lens holding member 10 is moved to the lens movement portion 39 of the attachment portion 35. Thus, the optical portion 21 of the lens 20 is received by the curved groove 39a of the lens movement portion 39, and the peripheral portion of the intraocular lens 20 comes into engagement with the reverse surfaces of the opening projection edges 39b (support portion guides 41) of the lens movement portion 39. As a result, the vertical position of the center of the optical portion 21 of the lens 20 coincides with the center axis of the push rod 33 substantially. However, the support portions 22a and 22b of the lens 20 are held in the space 40 by means of the support portion guides 41, whereby the optical portion 21 and the support portions 22a and 22b of the lens 20 are stably held in different spaces. Therefore, the optical portion 21 and the support portions 22a and 22b of the lens 20 have a stable positional relationship such that the support portions 22a and 22b are located above the optical portion 21. When the push rod 33 is advanced, the intraocular lens 20 is moved within the space 15 in a direction perpendicular to the page of FIG. 3B. The support portion guides 41 ends at an axial position in the vicinity of the distal end of the attachment portion 35 as shown in FIG. 3C, and the space 40 for receiving the support portions 22a and 22b ends at that axial position. Therefore, in the course of advance movement of the lens 20, the support portions 22a and 22b of the lens 20 move to the space 15 where the optical portion 21 of the lens 20 is present. In other words, the positional relationship between the optical portion 21 and the support portions 22a and 22b of the lens 20 changes along the direction of movement of the lens 20. Subsequently, the lens 20 is passed through the insertion tube 32 provided integrally with the attachment portion 35, and is then pushed into the eye. Since the positional relationship between the optical portion 21 and the support portions 22a and 22b of the lens 20 is maintained stably, the problem of the support portions 22a and 22b being deformed or broken can be prevented.

Since upon pressing of the push member 13 the protrusions 13c come into engagement with the depressions 14e, the intraocular lens 20 having been moved to the lens movement portion 39 is prevented from reassuming its original shape, and reliable positioning is effected.

The lens holding member 10 is preferably formed of transparent or semi-transparent material, which allows an operator to check whether the lens 20 has been moved to the lens movement portion 39.

Further, it becomes possible to check whether the space 15 for allowing movement of the intraocular lens 20 is formed between the lower surface of the top member 12 and the lens movement portion 39 of the attachment portion 35. In other words, the push member 13 of the top member 12 provides two functions; i.e., the function for moving the lens 20 downward and the function for forming the lens movement space 15 in cooperation with the attachment portion 35.

Figure 4A:
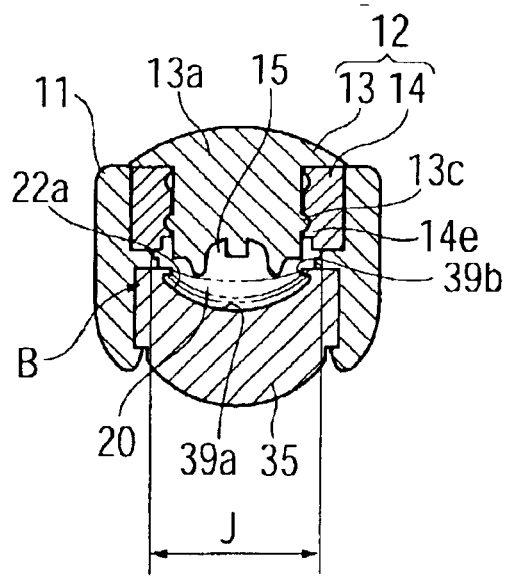
Figure 4B:
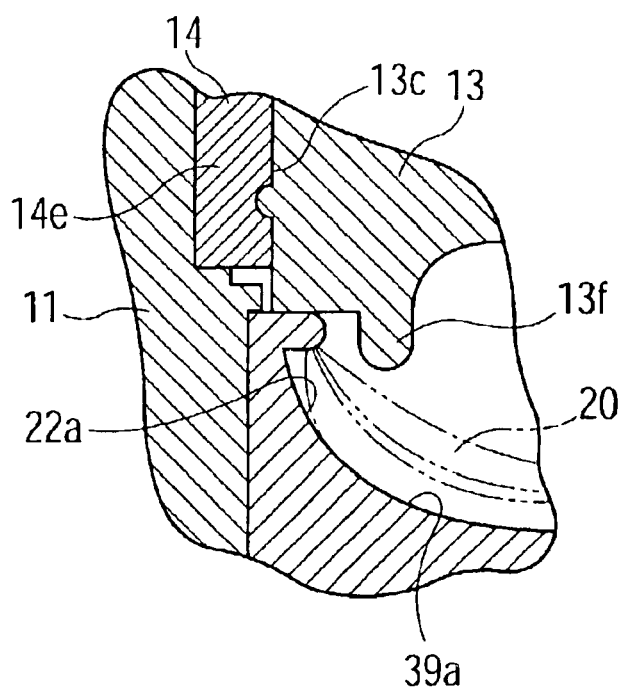

FIG. 4, which is an enlarged cross section corresponding to FIG. 3B, shows a conventional insertion device in which the optical portion 21 and the support portion 22a of the lens 20 are held in an unstable state. As shown in FIG. 4, the position of the support portion 22a may change randomly, so that the support portion 22a may be positioned above or below the optical portion 21, and the support portion 22a may be deformed or broken when the lens 20 is pushed out by means of the pusher mechanism 34.

As described above, the lens holding member 10 of the embodiment—which consists of the base member 11 and the top member 12 including the nipping member 14 and the push member 13—functions as a portion of the mechanism of the insertion device 30 upon attachment thereto.

In the above described embodiment, the tubular main body 31 of the insertion device 30 and the lens holding member 10 are assembled in order to complete the insertion device 30. However, the base member 11 may be formed integrally with the attachment portion 35 of the tubular main body 31. Further, the top member 12 may be formed integrally with the base member 11 such that the top member 12 is connected to one end portion of the upper surface of the base member 11 via a hinge.

Further, the present embodiment is characterized in that a portion of deforming means for deforming the intraocular lens 20 to a reduced size is formed integrally with the lens holding member 10.

That is, when the lens is moved to the lens movement portion 39 of the attachment portion 35, the lens is deformed to a reduced size. This size reduction is achieved by three design features; i.e., the lens movement portion 39 being formed into a form of a curved groove, the lens 20 being moved while be pressed toward the lens movement portion 39 by the top member 12, and the dimension J of the lens movement portion 39 being smaller than the dimension K of the lens 20.

Since such an intraocular-lens insertion device must be used in a germ-free environment, during actual use of the insertion device, an operator must use the device while wearing gloves, which hinders fine operation. Therefore, the above-described attachment method is preferable, because an operator can perform the operation of moving the intraocular lens 20 from the first or standby position to the second or insertion position by pressing the push member 13 of the lens holding member 10 from above and inserting the lens 20 from the insertion device 30 into the eye, while holding the insertion device 30, which is larger and easier to hold than the lens holding member 10.

In the above-described embodiment, the lens holding member 10 and the insertion tube 32 form deforming means for deforming the intraocular lens 20. However, the present invention is not limited thereto, and the configuration of the device may be modified to assume various configurations; e.g., a configuration such that only the lens holding member 10 is used to deform the intraocular lens 20 to a small size suitable for insertion into the eye, and the thus-deformed lens 20 is passed through the insertion tube 32 and inserted into the eye; and a configuration such that deforming means is not provided on the lens holding member 10, but is provided on the insertion tube 32.

In the specification, the term "center of the intraocular lens 20" refers to the center in the thickness direction located on the optical axis of the optical portion 21.

Obviously, numerous modifications and variations of the present invention are possible in light of the above teachings. It is therefore to be understood that within the scope of the appended claims, the present invention may be practiced otherwise than as specifically described herein.

What is claimed is:

1. An insertion system for an intraocular lens having a deformable optical portion and at least one loop-shaped support portion for supporting the optical portion within an eye, comprising:

holding means for holding the intraocular lens at a standby position in a state in which no stress acts on the optical portion of the lens;

deforming means for deforming the lens to a reduced size;

an insertion tube through which the deformed lens is inserted into the eye;

a pusher mechanism having a push rod for pushing and inserting the lens into the eye; and a lens moving mechanism for moving the lens from the standby position to an insertion position at which the pusher mechanism can push and insert the lens into the eye, wherein when the lens is moved to the insertion position by means of the lens moving mechanism, the optical portion and the support portion of the lens are placed in different spaces in order to fix the positional relationship between the optical portion and the support portion of the lens.

2. An insertion system according to claim 1, wherein the positional relationship between the optical portion and the support portion of the lens is changed along a direction of movement of the lens.

3. An insertion system according to claim 1, wherein when the lens is pushed out by means of the pushing mechanism, the optical portion and the support portion of the lens located in the different spaces move to a common space.

* * * * *